United States Patent
Matsuda et al.

(10) Patent No.: US 8,703,627 B2
(45) Date of Patent: *Apr. 22, 2014

(54) ANTIADHESIVE MATERIAL

(75) Inventors: Shojiro Matsuda, Ayabe (JP); Yoshimi Tanaka, Ayabe (JP); Yoshito Ikada, Uji (JP)

(73) Assignees: Gunze Limited, Kyoto (JP); JMS Co., Ltd., Hiroshima (JP)

( * ) Notice: Subject to any disclaimer, the term of this patent is extended or adjusted under 35 U.S.C. 154(b) by 585 days.

This patent is subject to a terminal disclaimer.

(21) Appl. No.: 10/480,744

(22) PCT Filed: Jun. 12, 2002

(86) PCT No.: PCT/JP02/05822
§ 371 (c)(1),
(2), (4) Date: Dec. 11, 2003

(87) PCT Pub. No.: WO02/102428
PCT Pub. Date: Dec. 27, 2002

(65) Prior Publication Data
US 2004/0137179 A1   Jul. 15, 2004

(30) Foreign Application Priority Data
Jun. 15, 2001   (JP) ................. 2001-182317

(51) Int. Cl.
*B32B 27/04* (2006.01)
*B32B 27/12* (2006.01)

(52) U.S. Cl.
USPC .......... 442/123; 442/312; 428/36.1; 606/228; 606/230; 606/231; 424/426; 424/444

(58) Field of Classification Search
USPC .......... 606/228, 230, 231; 442/123, 286, 394, 442/312; 428/36.1; 424/426, 444
See application file for complete search history.

(56) References Cited

U.S. PATENT DOCUMENTS 3,232,291 A * 2/1966 Parker .................. 602/75
4,374,063 A * 2/1983 Consolazio et al. ......... 530/355

(Continued)

FOREIGN PATENT DOCUMENTS

| EP | 0 734 736 | 10/1996 |
| EP | 0 745 394 | 12/1996 |

(Continued)

OTHER PUBLICATIONS

Japanese Office Action issued in Japanese Application No. 2003-406296, mailed Dec. 3, 2009 with a partial English Translation—4 pages.

*Primary Examiner* — Andrew Piziali
(74) *Attorney, Agent, or Firm* — Hamre, Schumann, Mueller & Larson, P.C.

(57) ABSTRACT

An antiadhesive material that is excellent in biocompatibility and bioabsorbability, as well as excellent strength in suturing and bonding, is provided. A reinforcing material 12 made of a biodegradable polymer is placed in a gelatin solution so that the reinforcing material 12 is impregnated with the solution, and the gelatin is caused to gelate and dried. By so doing, an antiadhesive material in which a gelatin film 11 and the reinforcing material 12 are integrated is obtained. The reinforcing material 12 preferably is arranged in a portion of the gelatin film 11 to be subjected to suturing, and preferably is arranged along a periphery of the gelatin film 11. The gelatin film 11 preferably is a cross-linked gelatin film, and the reinforcing material 12 preferably is a nonwoven fabric.

20 Claims, 9 Drawing Sheets

(56) References Cited

U.S. PATENT DOCUMENTS

| | | | |
|---|---|---|---|
| 5,447,940 A * | 9/1995 | Harvey et al. ............... 514/310 |
| 5,795,584 A * | 8/1998 | Totakura et al. ............. 424/444 |
| 5,854,381 A * | 12/1998 | Jurgens et al. .............. 424/444 |
| 6,001,895 A * | 12/1999 | Harvey et al. ............... 523/113 |
| 6,162,962 A * | 12/2000 | Hinsch et al. ............. 623/11.11 |
| 6,599,323 B2 | 7/2003 | Melican et al. |
| 6,737,371 B1 * | 5/2004 | Planck et al. ............... 442/304 |
| 2001/0016205 A1 | 8/2001 | Shimizu |
| 2006/0094318 A1 | 5/2006 | Matsuda et al. |

FOREIGN PATENT DOCUMENTS

| | | |
|---|---|---|
| EP | 1 022 031 | 7/2000 |
| EP | 1 084 686 | 3/2001 |
| EP | 1 098 024 | 5/2001 |
| EP | 1 201 202 | 5/2002 |
| JP | 63-160845 | 10/1988 |
| JP | 6-254148 | 9/1994 |
| JP | 8 317 968 | 12/1996 |
| JP | 10-113384 | 5/1998 |
| JP | 11-239610 | 2/1999 |
| JP | 2000-37450 | 2/2000 |
| JP | 2000-60956 | 2/2000 |
| JP | 2000-197693 | 7/2000 |
| JP | 2004-65780 | 3/2004 |
| WO | WO 9707833 A2 * | 3/1997 ............. A61L 31/00 |
| WO | 98/22157 | 5/1998 |
| WO | 99/63908 | 12/1999 |

* cited by examiner

ANTIADHESIVE MATERIAL

TECHNICAL FIELD

The present invention relates to an antiadhesive material for preventing tissues in a living body from adhering to each other, and more specifically, to an antiadhesive material that is excellent in biocompatibility, bioabsorbability, and strength in suturing.

BACKGROUND ART

In various clinical fields including cardiac surgery, orthopedics, neurosurgery, abdominal surgery, and obstetrics and gynecology, it has been a serious problem that after a surgical operation of various types or due to an external injury, tissues in an affected part in a living body adhere to one another. The adhesion of tissues, for instance, can cause pain or impair function, which, if serious, requires another surgical operation for separating the adhering tissues. Moreover, the adhesion also causes a problem of making a follow-up operation with respect to the primary disease difficult. To cope with these problems, conventionally, antiadhesive materials for covering and protecting tissues potentially subject to adhesion have been developed, for the purpose of preventing adhesion of tissues in a living body. A regenerated oxidized cellulose fabric, a hyaluronic acid-carboxymethyl cellulose mixture film, etc., have been in actual use as antiadhesive materials.

More specifically, in order for such an antiadhesive material to perform the antiadhesive function, it is necessary that the antiadhesive material should be present at an application site (affected part) at which adhesion possibly occurs during a required period of time so as to function as a barrier between tissues at the application site, be decomposed finally, and be absorbed in the body. In other words, the antiadhesive material is required to be excellent in biocompatibility, bioabsorbability, and the like.

Even in the case of such an antiadhesive material excellent in biocompatibility and the like as described above, it has to be fixed firmly at the application site so as to perform these functions sufficiently. As a fixing method for this purpose, normally, methods of suturing with a suture thread, bonding with an adhesive, and the like have been used.

DISCLOSURE OF THE INVENTION

However, the conventional antiadhesive material as described above has difficulty in, for instance, performing the antiadhesive function while maintaining its form in a living body for a required period of time, and since it does not have a strength sufficient for durability in suturing, bonding, or the like, it is torn in some cases. Thus, the handling of the antiadhesive material and the fixing of the same at an application site are difficult.

For instance, antiadhesive materials formed with gelatin films excellent in biocompatibility, bioabsorbability, etc., which recently have been studied and developed, and now are in actual use (for instance, JP 11(1999)-239610 A, JP 2000-37450 A, etc.) are inferior in allowing themselves to adhere and fix to surfaces of tissues at an application site. Therefore, for fixing the same at an application site, the suturing and/or bonding methods as described above are used. However, such gelatin films, when applied to tissues, absorb moisture of the tissues and become in a hydrogel state containing water. Therefore, they have a problem that they are difficult to fix by suturing, etc.

Therefore, it is an object of the present invention to provide an antiadhesive material that is excellent in biocompatibility and bioabsorbability, and has an excellent strength in suturing and bonding.

To achieve the foregoing object, an antiadhesive material of the present invention is an antiadhesive material formed with a gelatin film, and has a structure such that a reinforcing material made of a biodegradable polymer other than collagen is arranged in the gelatin film. In the present invention, the antiadhesive material refers to a "material for preventing adhesion of tissues in a living body", and the biodegradable polymer refers to a "polymer that is degraded and absorbed in a living body". It should be noted that in the present invention, the gelatin film may be, for instance, porous or nonporous.

With the present invention, a sufficient strength is imparted by reinforcing the gelatin film by arranging therein the reinforcing material made of a biodegradable polymer. Therefore, the antiadhesive material is easy to fix at an application site, and the fixed state can be maintained during a required period. This allows the adhesion prevention effect due to the gelatin film to be performed sufficiently at the application site. Further, since the reinforcing material is made of a biodegradable polymer with biocompatibility that is field-proven in the clinical medicine, a problem that it remains in a living body and causes a foreign body reaction with tissues, for instance, can be avoided. Therefore, the antiadhesive material of the present invention is particularly advantageous in the clinical field such as surgical operations.

In the antiadhesive material of the present invention, the reinforcing material preferably is arranged in a portion of the gelatin film to be subjected to suturing (hereinafter referred to as a suture portion). By arranging the same in the suture portion, an inconvenience that the gelatin film is torn by suturing can be avoided surely.

In the antiadhesive material of the present invention, since the prevention of adhesion is a function performed by the gelatin film, the portion other than the suture portion preferably is the gelatin film, and the reinforcing material preferably is arranged along a periphery of the gelatin film. The shape of the antiadhesive material of the present invention is not limited particularly, and apart from the sheet form, it may be in a cylindrical form.

In the antiadhesive material of the present invention, the reinforcing material preferably is a fabric body or a film body, and the film form may be, for instance, a porous film or a non-porous film.

In the antiadhesive material of the present invention, the arrangement of the gelatin film with the reinforcing material is not limited particularly. They may be integrated, for instance, by using an adhesive or the like, but it is preferable that the reinforcing material and the gelatin film are integrated due to the gelation of the gelatin that has intruded entirely or partially in an internal part of the reinforcing material. Thus, by gelating the gelatin in the internal part of the reinforcing material also, it is possible to carry out the formation of the gelatin into a film form and the integration concurrently. Additionally, the manufacture is facilitated further more since a specific step for integrating the gelatin film with the reinforcing material by using another means such as an adhesive is unnecessary, and they are integrated firmly.

In the antiadhesive material of the present invention, the foregoing fabric body as the reinforcing material is not limited particularly, but it preferably is a nonwoven fabric, a woven fabric, a knitted fabric, or a braid, more preferably, at least one complex selected from the group consisting of a complex of a nonwoven fabric and a woven fabric, a complex of a nonwoven fabric and a knitted fabric, and a complex of a nonwoven fabric and a braid.

The foregoing nonwoven fabric preferably is a nonwoven fabric manufactured by, for instance, melt blowing, needle punching, spunbonding, flash spinning, or the like.

In the antiadhesive material of the present invention, the foregoing fabric body preferably is processed by hot pressing. The hot pressing improves the binding of fibers and prevents fuzzing.

The property and shape of the foregoing fabric body are not limited particularly, but the fabric body preferably has a density in a range of 5 g/m$^2$ to 200 g/m$^2$ since a sufficient strength is obtained, and preferably has a thickness in a range of 10 μm to 500 μm.

The fabric body preferably has a yarn threading tension in a range of 0.3 N to 200 N. The yarn threading tension is determined by, for instance, the following method.
(Method for Measuring the Yarn Threading Tension)

A sample (5 mm×50 mm) is prepared, and ends of the sample in its lengthwise direction are fixed so that a distance between two chucks is 20 mm. Next, a 3-0 nylon suture with needle (Nesco Suture, ½ circle round-bodied needle) (trade name: Nesco Suture, manufactured by AZWELL Inc.) is threaded through the sample at a midpoint in the lengthwise direction and 2 mm from an edge in its width direction, and ends of the suture are fixed at a distance of 50 mm from the point at which the suture is threaded. Then, with the sample being maintained in the fixed state, the ends of the suture are pulled at a rate of 100 mm/min, and a maximal force (yarn threading tension) is measured using a measuring device (trade name: Instron 4302, manufactured by Instron Corporation).

In the antiadhesive material of the present invention, the film body as the reinforcing material is not limited particularly, and a film body manufactured by a normal known method such as pressing, casting, extruding, or the like may be used as the foregoing film body. The film body preferably has a thickness, for instance, in the same range as that of the fabric body.

In the antiadhesive material of the present invention, the biodegradable polymer preferably is at least one polymer selected from the group consisting of polylactic acid, lactic acid-caprolactone copolymer, and polyglycolic acid. Among these, it preferably is polylactic acid and/or lactic acid-caprolactone copolymer since it exhibits an appropriate degradability and absorbability when it forms the reinforcing material.

In the antiadhesive material of the present invention, the foregoing reinforcing material preferably is treated so that hydrophilicity is imparted thereto. By imparting hydrophilicity to a surface of the reinforcing material, excellent integration of the reinforcing material with the gelatin film is achieved, thereby hardly causing the reinforcing material to separate from the gelatin film. Examples of the method for imparting hydrophilicity include plasma treatment, glow discharge treatment, corona discharge treatment, ozone treatment, graft treatment, coating, chemical treatment, ultraviolet irradiation, etc. Among these, plasma treatment is preferable.

In the antiadhesive material of the present invention, the gelatin film preferably is a cross-linked film that is cross-linked so as to be, for instance, degraded in a living body after a desired period of time lapses. This is because, as described above, the antiadhesive material is required to be present at an application site during a required period of time and perform an antiadhesive function, and after the period lapses, it is required to be degraded and absorbed in the living body so that a foreign body reaction with tissues therein should be avoided. It should be noted that as the degree of cross-linkage of the gelatin film is relatively higher, it indicates that the degradation of the same in a living body is slower.

In the antiadhesive material of the present invention, the gelatin film preferably is cross-linked by at least one method selected from ultraviolet treatment, heat treatment, chemical cross-linking agent treatment, and other means.

In the antiadhesive material of the present invention, the gelatin film preferably is cross-linked under conditions of an ultraviolet lamp of 4 W to 40 W, an irradiation time of 0.1 hour to 100 hours, and an irradiation distance of 5 cm to 100 cm. It should be noted that the ultraviolet irradiation exhibits a degree of cross-linkage that varies depending on various conditions, for instance, the ultraviolet intensity, that is, the power of the ultraviolet lamp, the irradiation time, the irradiation distance, etc. Therefore, the foregoing conditions may be determined appropriately according to a desired degradation time of the gelatin film.

In the antiadhesive material of the present invention, a time of presence of the gelatin film in a living body preferably is in a range of 12 hours to 30 days. In the present invention, the "time of presence in a living body" refers to a time that lapses from the application of the antiadhesive material in a living body until the degradation and absorption of the gelatin film in the living body (hereinafter it also is referred to as a "degradation time"). It should be noted that even the same gelatin film exhibits a different time of presence in a living body depending on the organ to which the gelatin film is applied. Therefore, the time of presence in a living body preferably is set according to the application site.

In the antiadhesive material of the present invention, the gelatin film preferably has a thickness in a range of 20 μm to 2000 μm from the viewpoint of handlability.

Since the antiadhesive material of the present invention is applied in a living body, a concentration of endotoxin contained in the gelatin preferably is more than 0 and not more than 200 EU/g, more preferably, not more than the detection limit, so that the safety is secured. It should be noted that ideally no endotoxin is contained, that is, the content of endotoxin is zero, but this is not practical. Therefore, the lower limit thereof is described to be "more than 0". Further, it is preferable that the antiadhesive material of the present invention substantially does not contain other toxic substances, or that contents of the same are within legally or medically tolerable ranges.

BRIEF DESCRIPTION OF DRAWINGS

FIG. 8A is a plan view of the same, FIG. 8B is a perspective view of the same, and FIG. 8C is a perspective view of a sample cut out of the antiadhesive material.

DESCRIPTION OF THE INVENTION

Figure 1:
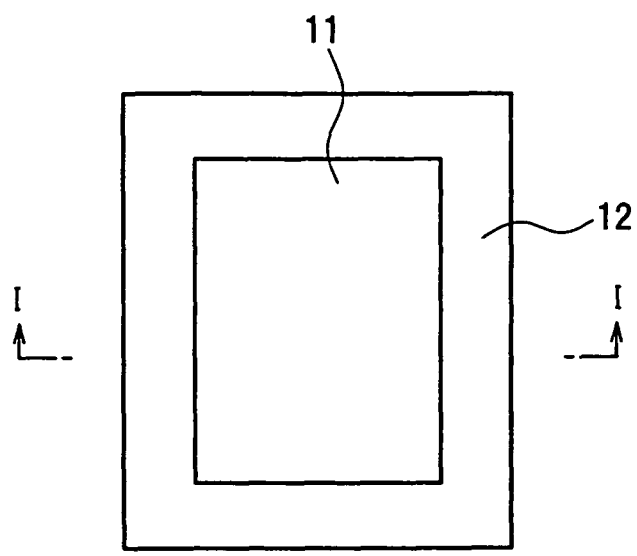
FIG. 1 is a plan view illustrating an example of an antiadhesive material of the present invention.

Though the degradation time of the gelatin film varies with the application site, as described above, the gelatin film of the present invention preferably is degraded in, for instance, 12 hours to 90 days, more preferably in a range of 1 day to 30 days, particularly preferably in a range of 2 days to 7 days. In the case where the degradation time is not less than 12 hours, it is possible to prevent the adhesion of tissues sufficiently, and in the case where the degradation time is not more than 90 days, particularly not more than 30 days, it is possible to prevent adhesion sufficiently, while the gelatin film does not cause a reaction other than the adhesion prevention (for instance, the foreign body reaction, etc.) at the application site. The degradation time may be set by a cross-linking treatment that will be described later.

The thickness of the gelatin film can be determined appropriately according to, for instance, the application site, the desired degradation time of the gelatin film, etc., and it is, for instance, in a range of 20 μm to 2000 μm, preferably in a range of 30 μm to 500 μm, more preferably in a range of 50 μm to 200 μm. The thickness of the gelatin film of, for instance, not less than 20 μm leads to a further improved strength, and the thickness thereof of not more than 2000 μm leads to a further improved flexibility, thereby making the gelatin film easy to handle.

The foregoing gelatin film has a water content measured by a method described below of, for instance, 70% to 99%, preferably 75% to 97.5%, more preferably 80% to 95%. It should be noted that the water content indicates that, for instance, as it is relatively lower, the degradation of the gelatin film in a living body is slower. In the case where the gelatin film is obtained by cross-linking, the water content indicates that as it is relatively lower, the degree of cross-linkage is higher and the degradation of the same in a living body is slower.

The water content is measured in the following manner, for instance. First, the film is immersed in water at 25° C. for 12 hours, and thereafter, the wet weight thereof is measured. Subsequently, the film is dried completely with a vacuum dryer, and the dry weight of the film thus dried is measured. Then, the water content is calculated by substituting the foregoing weights in an equation shown below:

water content (%)=100×(wet weight−dry weight)/(wet weight)

Examples of a material for the gelatin film include, for instance, gelatins extracted from bones, tendons, skins, combs, etc. of mammals and bird species such as cow, pig, horse, fowl, etc. Such a gelatin may be prepared by, for instance, extracting from the foregoing animals, but normally, a commercially available product can be used. A method for the extraction is not limited particularly, and examples of the same include conventionally known acid treatment, alkali treatment, etc.

As the commercially available gelatin, for instance, an alkali-treated gelatin is preferable that contains only a very small amount of endotoxin and that is therefore excellent in safety. More specifically, examples of the same include a cow-originated alkali-treated gelatin and a pig-originated acid-treated gelatin manufactured by Nippi Inc., and the like.

Further, as materials for the gelatin film, apart from gelatin, additives may be used. Examples of the additives include glycerin, polyethylene glycol, and hyaluronic acid for imparting flexibility to the film, as well as antimicrobial agents, anti-inflammatory agents, etc.

The gelatin film can be manufactured by forming gelatin in a film form by, for instance, casting, extruding, or another method, among which casting is used preferably.

The film formation by casting can be carried out by, for instance, the following manner.

First, gelatin as a material is dissolved in a solvent in a heated state. As the solvent, for instance, distilled water, dimethyl sulfoxide (DMSO), etc., and mixture solutions of these can be used. Among these, distilled water is preferable from the viewpoint of handlability. The proportion of gelatin added per 100 ml of a solvent is, for instance, in a range of 0.1 g to 50 g, preferably in a range of 1 g to 30 g, more preferably in a range of 5 g to 20 g. The temperature for dissolution is, for instance, in a range of 10° C. to 80° C., preferably in a range of 30° C. to 70° C., more preferably in a range of 40° C. to 60° C. Further, the dissolution time is not limited particularly as long as the gelatin is dissolved, and for instance, it is in a range of 1 minute to 100 hours, preferably in a range of 5 minutes to 50 hours, more preferably in a range of 10 minutes to 24 hours.

In the case where additives other than gelatin as mentioned above are contained, the proportion of the additives added per 1 g of gelatin is, for instance, in a range of 1 mg to 20 g, preferably in a range of 5 mg to 10 g, more preferably in a range of 10 mg to 5 g.

Such a gelatin solution is cast in a petri dish, and is dried, whereby a gelatin film is produced. The size of the petri dish is not limited particularly, and may be set according to desired length, width, thickness, etc. of a film, or alternatively, after forming a film, the film may be cut into a desired size before use.

The gelatin solution preferably is cast, for instance, in a range of 0.01 ml to 3 ml per unit area ($cm^2$) of a petri dish, more preferably in a range of 0.03 ml to 1 ml, particularly preferably in a range of 0.05 ml to 0.5 ml.

The drying can be carried out, for instance, under a condition of natural drying, heat drying, reduced-pressure drying (vacuum drying), forced exhaust drying, forced-circulated convection, or the like. More specifically, a drying temperature is, for instance, in a range of −40° C. to 90° C., preferably in a range of 0° C. to 50° C., more preferably in a range of 10° C. to 30° C. A drying time is, for instance, in a range of 1 hour to 100 hours, preferably in a range of 3 hours to 50 hours, more preferably in a range of 5 hours to 24 hours.

The foregoing series of film forming steps preferably is carried out aseptically, for instance, on a clean bench, or in a clean room. This is intended to prevent the gelatin film from being contaminated by various germs breeding during the steps. Therefore, it is preferable to use manufacturing equipment sterilized, for instance, by using an autoclave, by using ethylene oxide gas (EOG), by hot-air sterilization, by applying electron beams, etc. Further, the gelatin solution also preferably is subjected to the foregoing steps after it is sterilized by, for instance, conventional known filtering sterilization.

The gelatin film thus obtained may be used as it is, but it preferably is cross-linked further, since by so doing the degradation time thereof in a living body can be set desirably, as described above.

Examples of an applicable cross-linking method include ultraviolet (UV) irradiation, heat treatment, treatment using a chemical cross-linking agent, etc. Examples of the chemical cross-linking agent include aldehydes, epoxies, carbodiimides, isocyanates, tannin, chromium, etc. Examples of aldehyde include formaldehyde, glutaraldehyde, acid aldehyde, glyoxal, dialdehyde malonate, dialdehyde succinate, aldehyde phthalate, dialdehyde starch, polyacrolein, polymethacrolein, etc. Examples of epoxy include glycerol diglycidyl ether, sorbitol diglycidyl ether, ethylene glycol diglycidyl ether, polyethylene glycol diglycidyl ether, polyglycerol polyglycidyl ether, etc. Examples of carbodiimide include water-soluble carbodiimides (for instance, 1-ethyl-3-(3-dimethylaminopropyl)carbodiimide, cyclohexyl-3-(2-morpholinoethyl)carbodiimide, etc.), dicyclohexyl carbodiimide, etc. The type of the chemical cross-linking agent used is not limited particularly as long as the gelatin is cross-linked, and, for instance, one type may be used alone, or two or more types may be used in combination.

Among the foregoing cross-linking methods, UV irradiation is preferable. UV irradiation makes it possible to achieve easily a cross-linked gelatin film that has more excellent effects such as being degradable in a living body in a relatively short time, leaving no toxic chemical substance of a low molecular weight, and hardly causing deformation of a product.

In the case where the cross-linking is carried out by UV irradiation, conditions of, for instance, power of an UV lamp, an irradiation time, an irradiation distance, etc. can be set appropriately according to a desired degradation time of the gelatin film. The power of an UV lamp is, for instance, in a range of 4 W to 40 W, preferably in a range of 8 W to 30 W, more preferably in a range of 12 W to 20 W. The irradiation time is, for instance, in a range of 0.1 hour to 100 hours, preferably in a range of 0.5 hour to 60 hours, more preferably in a range of 1 hour to 50 hours. The irradiation distance is, for instance, in a range of 5 cm to 100 cm, preferably in a range of 10 cm to 90 cm, more preferably in a range of 20 cm to 80 cm.

More specifically, for instance, in the case where the power of a LUV lamp is in a range of 4 W to 40 W, the irradiation time and the irradiation distance preferably are in a range of 0.1 hour to 100 hours and in a range of 5 cm to 100 cm, respectively. More preferably, in the case where the power of a UV lamp is in a range of 8 W to 30 W, the irradiation time and the irradiation distance are in a range of 0.5 hour to 60 hours and in a range of 10 cm to 90 cm, respectively. Particularly preferably, in the case where the power of an UV lamp is in a range of 12 W to 20 W, the irradiation time and the irradiation distance are in a range of 1 hour to 50 hours and in a range of 20 cm to 80 cm, respectively.

Particularly, a cross-linked gelatin film prepared under conditions of the power of an UV lamp of 15W, the irradiation time of 5 hours to 30 hours, and the irradiation distance of 30 cm to 70 cm was proven to be more excellent in degradability, safety, strength, etc. by experiments conducted by the inventors. More specifically, for instance, a cross-linked gelatin film with a thickness of 100 μm that was cross-linked under conditions of the power of an UV lamp of 15W, the irradiation time of 20 hours, and the irradiation distance of 60 cm degraded and disappeared in about one week in the case where it was sutured in an abdominal cavity of a rat, and in about four weeks in the case where it was sutured to a pericardial sac of a dog. This proves that the cross-linked gelatin films prepared under the foregoing conditions so as to have desired degradation times according to a variety of application sites have excellent utility, particularly in the clinical medicine.

Next, since the reinforcing material of the present invention is intended for reinforcing the gelatin film, it need not remain in a body after the gelatin film performs its function and is degraded and absorbed, and in order that the reinforcing material should be prevented from remaining in a body and causing an unnecessary foreign body reaction with tissues at an application site, it is necessary that the reinforcing material should be degraded and absorbed. For this purpose, a fabric body, a film body, or the like made of a biodegradable polymer as described above is used.

It should be noted that the reinforcing material may be composed of a single layer, or a laminate including two or more layers. In the case where it is a laminate, it may be composed of fabric bodies or film bodies of one kind, or alternatively, it may be composed of fabric bodies or film bodies of two or more kinds, for instance.

The reinforcing material is not limited particularly as long as it does not remain in a living body as described above, but since it is used for a reinforcing purpose, it desirably has some strength and flexibility, and additionally, degradability. Further, it preferably has biocompatibility based on usage in the clinical medicine, and causes few foreign body reactions and inflammations. Therefore, examples of the foregoing biodegradable polymer include, as described above, polylactic acid, lactic acid-caprolactone copolymer, polyglycolic acid, lactic acid-glycolic acid copolymer, lactic acid-ethylene glycol copolymer, polydioxanon, glycolic acid-caprolactone copolymer, glycolic acid-trimethylene carbonate copolymer, glycolic acid-dioxanon-trimethylene carbonate copolymer, chitin, chitosan, fibrin, etc. Preferably, polylactic acid, lactic acid-caprolactone copolymer, or polyglycolic acid is used.

Examples of the form of the foregoing fabric body include a woven fabric, a nonwoven fabric, a knitted fabric, a braid such as flat braid, etc., as described above. Among these, a nonwoven fabric is particularly preferable since it has a structure in which fine fibers tangle with one another highly, and hence, it does not have an orientation, allows the thickness to be set easily, and provides excellent flexibility. A knitted fabric and a woven fabric are particularly preferable since they are further excellent in ease of setting a thickness, flexibility, strength, and yarn threading tension. Furthermore, a material (a complex) obtained by integrating a nonwoven fabric with any one of a knitted fabric, a woven fabric, and a braid is particularly preferable since it has the foregoing advantages of the both together.

In the case where the reinforcing material is the fabric body described above, the yarn threading tension preferably is, for instance, in a range of 0.3 N to 200 N, more preferably in a range of 0.4 N to 150 N, particularly preferable in a range of 0.5 N to 100 N. It should be noted that this value can be determined by the above-described method.

The density of the fabric body is, for instance, in a range of 5 g/m$^2$ to 200 g/m$^2$, preferably in a range of 8 g/m$^2$ to 80 g/m$^2$, more preferably in a range of 10 g/m$^2$ to 60 g/m$^2$.

The fabric body is determined appropriately according to the size and desired strength of the gelatin film, and has a thickness, for instance, in a range of 10 μm to 1000 μm, preferably in a range of 20 μm to 800 μm, more preferably in a range of 30 μm to 600 μm. Further, in the case where the fabric body is a laminate as described above, it preferably has a thickness, for instance, in a range of 10 μm to 1000 μm, more preferably in a range of 20 μm to 800 μm, particularly preferably in a range of 30 μm to 600 μm. It should be noted that this applies to the film body as a reinforcing material.

The nonwoven fabric can be prepared by, for instance, melt blowing, needle punching, spunbonding, or flash spinning as a conventionally known process, or the like. Among these, the melt blowing is particularly preferable since it does not require the use of a solvent, and manufactures a thin fabric easily by decreasing diameters of fibers and tangling thin fibers highly.

The melt blowing is a method for manufacturing a web of self-adhesive microfibers by, for instance, blowing a molten material from a die of an extruder onto an accumulating screen with high speed airflow so that pieces of the material thus blown cross and tangle.

In the case where a nonwoven fabric made of the polylactic acid or the polyglycolic acid is manufactured, a polymer obtained by polymerizing lactide or glycolide as a material is used. In the case where a nonwoven fabric made of the lactic acid-caprolactone copolymer is manufactured, a copolymer obtained by mixing and polymerizing lactide or caprolactone is used. In the latter case, a molar ratio (A:B) of lactide (A) and caprolactone (B) is, for instance, in a range of 85:15 to 40:60, preferably in a range of 82:18 to 42:58, more preferably in a range of 80:20 to 45:55.

The fabric body of the nonwoven fabric or the like thus prepared by the method as described above can be used as it is, as a reinforcing material in the antiadhesive material of the present invention, but it preferably is subjected further to hot pressing so that Tinting such as fuzzing is prevented as described above, and the binding of fibers is improved.

The hot pressing may be carried out, for instance, immediately after the formation of a web of a nonwoven fabric, or after the vacuum heat drying. It should be noted that the foregoing treatment preferably is applied to both sides of the reinforcing material such as the nonwoven fabric.

In the case where the hot pressing is carried out immediately after the formation of a web, it is carried out under conditions of, for instance, a temperature in a range of 65° C. to 95° C. and a pressure in a range of 0.01 MPa to 5 MPa, preferably a temperature in a range of 70° C. to 85° C. and a pressure in a range of 0.05 MPa to 2 MPa, more preferably a temperature in a range of 75° C. to 80° C. and a pressure in a range of 0.1 MPa to 1 MPa.

On the other hand, in the latter case, first, the vacuum heat drying is carried out, for instance, under the following conditions. A drying temperature is, for instance, in a range of 40° C. to 135° C., preferably in a range of 50° C. to 125° C., more preferably in a range of 60° C. to 115° C. Further, a drying time is, for instance, in a range of 1 hour to 70 hours, preferably in a range of 5 hours to 50 hours, more preferably in a range of 10 hours to 30 hours.

Subsequently, the hot pressing preferably is carried out under the following conditions. For instance, the conditions are, for instance, a temperature in a range of 80° C. to 110° C. and a pressure in a range of 0.01 MPa to 5 MPa, preferably a temperature in a range of 85° C. to 105° C. and a pressure in a range of 0.05 MPa to 2 MPa, more preferably a temperature in a range of 90° C. to 100° C. and a pressure in a range of 0.1 MPa to 1 MPa. If the heating temperature is not lower than 80° C., fuzzing can be eliminated sufficiently, while if the heating temperature is not higher than 110° C., excellent flexibility can be maintained.

Also in the case where the reinforcing material is, for instance, a two or more layers laminate composed of two or more fabric bodies as described above, the hot pressing may be applied after the fabric bodies are laminated so that the fabric bodies are integrated.

Further, the reinforcing material preferably is subjected to a hydrophilicity imparting treatment so that the adhesivity of the reinforcing material with the gelatin film is improved. Examples of the hydrophilicity imparting treatment include plasma treatment, glow discharge treatment, corona discharge treatment, ozone treatment, graft treatment, coating, chemical treatment, ultraviolet irradiation, etc., as described above. Among these, plasma treatment is preferable particularly.

Conditions for plasma treatment are not limited particularly, and the treatment preferably is carried out, for instance, in an oxygen atmosphere at a pressure of 1.33 Pa to 1330 Pa, at a temperature in a range of 0° C. to 100° C., with a power in a range of 5 W to 200 W, more preferably in an oxygen atmosphere at a pressure of 5 Pa to 500 Pa, at a temperature in a range of 10° C. to 50° C., with a power in a range of 10 W to 100 W. A treatment time may be, for instance, in a range of 1 second to 1000 seconds, preferably in a range of 3 seconds to 600 seconds.

In the foregoing plasma treatment, for instance, air, nitrogen, argon, helium, ammonia, carbon oxide, or water vapor may be used, apart from the foregoing oxygen gas.

The antiadhesive material of the present invention has a structure obtained by arranging the reinforcing material on the gelatin film as described above, and its shape and size are not limited particularly and can be determined appropriately, for instance, according to an application site. For instance, it has an overall length in a range of 0.5 cm to 50 cm, an overall width of 0.3 cm to 20 cm, and an overall thickness of 20 μm to 2000 μm. Preferably, it has an overall length in a range of 0.7 cm to 30 cm, an overall width of 0.4 cm to 15 cm, and an overall thickness of 30 μm to 500 μm. More preferably, it has an overall length in a range of 1 cm to 20 cm, an overall width of 0.5 cm to 10 cm, and an overall thickness of 50 μm to 200 μm.

A size of the reinforcing material is determined appropriately according to, for instance, an application site and a size of the gelatin film. A position in the gelatin film at which the reinforcing material is arranged is not limited particularly, but since the antiadhesive function is performed by the gelatin film in the antiadhesive material of the present invention, the reinforcing material preferably is integrated with the gelatin film in a smallest possible area that provides sufficient reinforcement for the suture, the bonding with an adhesive, or the like. Therefore, as described above, the reinforcing material preferably is arranged in a suture portion of the gelatin film, and the reinforcing material (a nonwoven fabric, a film, etc.) preferably is arranged only along a periphery of the gelatin film.

More specifically, in the case where the gelatin film has a length of 0.5 cm to 50 cm, a width of 0.3 cm to 20 cm, and a thickness of 20 μm to 2000 μm, the reinforcing material preferably is arranged along a periphery thereof, with a width in a range of 1 mm to 30 mm, more preferably with a width in a range of 1.5 mm to 20 mm, particularly preferably with a width in a range of 2 mm to 10 mm. Further, it preferably has a thickness in a range of 10 μm to 1000 μm, more preferably in a range of 20 μm to 800 μm, particularly preferably in a range of 30 μm to 600 μm.

The foregoing antiadhesive material, in its portion in which the reinforcing material is arranged on the gelatin film, preferably has the above-described yarn threading tension, for instance, in a range of 0.20 N to 200 N, more preferably in a range of 0.25 N to 150 N, particularly preferably in a range of 0.30 N to 100 N.

As a method for arranging the reinforcing material on the cross-linked gelatin film, for instance, the following five methods are available. It should be noted that these methods refer to a case where an antiadhesive material having a reinforcing material 12 arranged only along a periphery of a gelatin film 11 as shown in the plan view (top view) of FIG. 1 is manufactured.

The first method is as follows. First, the gelatin solution is cast in a petri dish as described above, and a reinforcing material in a square frame form as shown in FIG. 1 is immersed therein so that an internal part of the reinforcing material is impregnated with the gelatin solution. In this case, it is preferable that the reinforcing material is subjected to a hydrophilicity imparting treatment, or that the gelatin solution is deaerated, so that the internal part is impregnated with the gelatin solution sufficiently. Then, the gelatin is caused to gelate, and is dried as described above. This causes the gelatin in the reinforcing material to gelate as well, concurrently with the formation of a gelatin film, whereby an antiadhesive material is prepared in which the gelatin film 21 and the reinforcing material 22 including the gelating gelatin therein are integrated with each other, as shown in the cross-sectional view of FIG. 2 (cross-sectional view taken along an arrow line I-I shown in FIG. 1). It should be noted that dots in the foregoing drawing schematically represent the gelatin, so as to indicate the presence of the gelating gelatin in the non-woven fabric, and this applies to FIGS. 3 and 4.

The second method is as follows. First, the gelatin solution is cast in the petri dish, and the gelatin is caused to start gelating. Then, before the gelatin gelates completely, a reinforcing material in a square frame form is placed on the gelatin in a state immediately before gelation. The gelatin is caused to gelate completely, and is dried. Since this causes the gelatin solution to infiltrate in the reinforcing material partially, the gelatin gelates in the reinforcing material, concurrently with the formation of a gelatin film, whereby an antiadhesive material is prepared in which the reinforcing material 32 and the gelatin film 31 are integrated with each other, as shown in the cross-sectional view of FIG. 3.

This method does not require, for instance, the deaeration or the like for impregnating the reinforcing material with the gelatin solution sufficiently, and therefore, it enables the integration more easily as compared with the first method.

Figure 4:
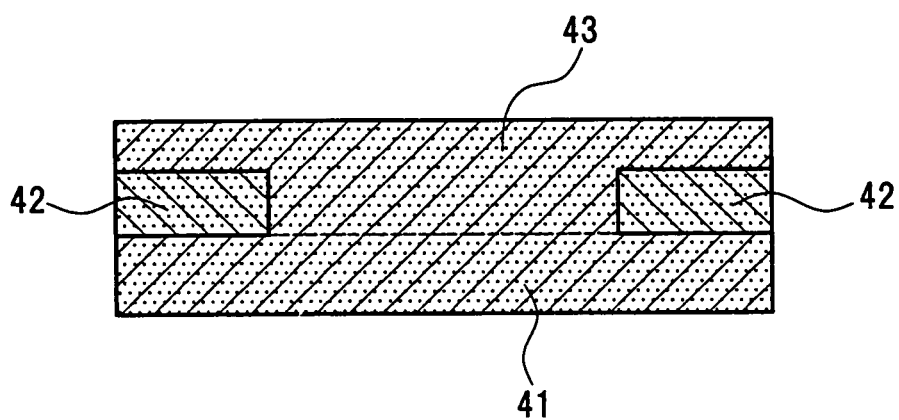
FIG. 4 is a cross-sectional view illustrating still another example of an antiadhesive material of the present invention.

The third method is a method in which, for instance, a complex composed of the reinforcing material and the gelatin film that have been integrated by the second method is immersed in the gelatin solution in a manner such that the reinforcing material faces the gelatin solution. This provides an antiadhesive material structured so that the reinforcing material 42 is embedded in gelatin films 41 and 43, as shown in FIG. 4. It should be noted that in the drawing, the gelatin films 41 and 43 are integrated by the second gelation. In the antiadhesive material of such a structure, for instance, the reinforcing material is not exposed on a surface thereof. Therefore, it is possible to bring the gelatin film in contact with an entire area of an application site.

The fourth method is as follows. A nonwoven fabric in a desired shape is held between glass plates that are opposed to each other so that they have a desired thickness beforehand, and the gelatin solution is poured between the glass plates. Then, it is cooled so as to gelate, and thereafter, it is dried. In this case also, the gelatin solution infiltrates in the reinforcing material partially, and thereafter gelates. As a result, an antiadhesive material in which reinforcing material and the gelatin film are integrated with each other can be obtained. Further, since the reinforcing material is not exposed on a surface thereof, as in the antiadhesive material obtained by the third method, it is possible, for instance, to bring the gelatin film in contact with an entire area of an application site.

The foregoing methods utilize the infiltration of the gelatin solution in the reinforcing material so that the gelatin gelates also in an entirety or part of an internal part of the reinforcing material. Therefore, the methods allow for sufficient integration of the gelatin film and the reinforcing material, and an antiadhesive material thus obtained does not undergo, for instance, the separation of the reinforcing material during use, and is capable of maintaining an excellent strength with respect to the suturing and the like of the antiadhesive material. It should be noted that the integration is not limited by the above-described methods, and it may be achieved by, for instance, using an adhesive or the like. Further, after the integration, the above-described cross-linking treatment may be applied. Still further, the present invention is not limited to an embodiment in which a reinforcing material is arranged in a part of a gelatin film as described above, but may take an embodiment in which a reinforcing material is arranged over an entire surface of a gelatin film.

Further, though the antiadhesive material of the present invention, in which the reinforcing material is arranged on the gelatin film as described above, may be used in a sheet form as it is, it alternatively may be formed, for instance, in a cylindrical shape beforehand (this antiadhesive material hereinafter referred to as a "cylindrical antiadhesive material").

Such a cylindrical antiadhesive material can be used, for instance, as an antiadhesive material for a tendon or a nerve, or an induction tube for a nerve. More specifically, for instance, in a state in which both ends of a cut nerve are inserted in the cylinder of the cylindrical antiadhesive material, the nerve and suture portions of the cylindrical antiadhesive material (portions at which a reinforcing material is arranged) are sutured.

Figure 5:
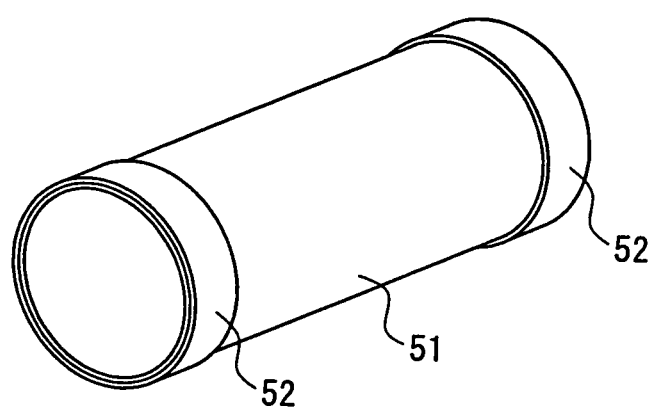
FIG. 5 is a perspective view illustrating still another example of an antiadhesive material of the present invention.

The cylindrical antiadhesive material has a structure in which, for instance, reinforcing materials 52 are arranged along circumferences of both ends (ends in an axial direction) of a gelatin film 51 in a cylindrical shape, as shown in the perspective view of FIG. 5. The size thereof is not limited particularly, and can be determined appropriately according to, for instance, an application site. For instance, it has an overall length in a range of 0.3 cm to 30 cm and an inside diameter in a range of 1 mm to 1 cm, and the gelatin film and the reinforcing material have thicknesses as those described above, respectively.

The cylindrical antiadhesive material as described above can be prepared, for instance, by the following method. First, a rectangular gelatin film is prepared, and reinforcing materials are arranged on both ends in its width direction and both ends in its lengthwise direction. Then, this is rolled so as to have a cylindrical shape, and the ends in the width direction of the gelatin film are overlapped at the positions where the reinforcing materials are arranged, and are bonded with an adhesive or sutured with a bioabsorbable suture thread. Thus, a cylindrical antiadhesive material is obtained. It should be noted that in the antiadhesive material of the present invention, the reinforcing material may be arranged on an internal surface or an external surface of the gelatin film in the cylindrical shape, but considering that the gelatin film provides the adhesion prevention effect and that ends of a cut nerve or the like are inserted in the cylinder, the reinforcing material 52 preferably is arranged on an external surface of the gelatin film 51 as shown in FIG. 5.

The method for manufacturing the cylindrical antiadhesive material is not limited to the above-described manufacturing method. For instance, it may be manufactured by rolling a gelatin film into a cylindrical form and bonding with an adhesive, the above-described gelation of the gelatin, or the like so as to form a cylindrical body, and thereafter, arranging the reinforcing materials at ends thereof. Alternatively, it can be obtained by placing a gelatin and a reinforcing material in a cylindrical mold, causing the gelatin to gelate, and subsequently drying the same.

Figure 6:
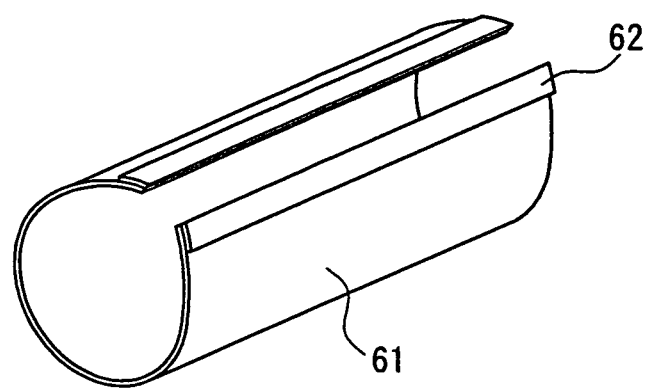
FIG. 6 is a perspective view illustrating still another example of an antiadhesive material of the present invention.

Still further, even the antiadhesive material in a sheet form as described above also can be used as a cylindrical body when it is used. For instance, as shown in the perspective view of FIG. 6, an antiadhesive material in which reinforcing materials 62 are arranged at ends of the gelatin film 61 in the width direction is rolled, and after a cut tendon or the like is sutured, the antiadhesive material is wrapped around the suture portion so as to cover the portion, and is sutured at the portions where the reinforcing materials 62 are arranged. By so doing, it can be used as a cylindrical body.

EXAMPLES

Example 1

Manufacture of Nonwoven Fabric-1

A nonwoven fabric was prepared using poly-L-lactic acid having a weight-average molecular weight (MW) of 950,000 as a material, by melt blowing using a general-purpose small extruder with a screw diameter of 20 mm. A melt blow die was composed of 126 nozzles (150 mm width) with a nozzle diameter of 0.3 mm. Air in a hopper was purged using nitrogen gas, and spinning was carried out at a nozzle temperature of 250° C. By adjusting a discharged amount using a gear pump as well as a speed of a belt conveyer so as to control a laminated amount, two kinds of nonwoven fabrics, that is, a nonwoven fabric A (density: 20 g/m$^2$, thickness: 200 μm), and a nonwoven fabric B (density: 35 g/m$^2$, thickness: 350 μm) were manufactured. These nonwoven fabrics were subjected to vacuum drying at 105° C. for 20 hours, so that residual monomers were removed and the crystallization was promoted.

Manufacture of Nonwoven Fabric-2

A nonwoven fabric was prepared using L-lactic acid-ε-caprolactone copolymer having a weight-average molecular weight (MW) of 400,000 (copolymerization ratio (molar ratio) L-lactide: ε-caprolactone=75:25) as a material, by melt blowing using a general-purpose small extruder with a screw diameter of 20 mm. A melt blow die was composed of 126 nozzles (150 mm width) with a nozzle diameter of 0.3 mm. Air in a hopper was purged using nitrogen gas, and spinning was carried out at a nozzle temperature of 270° C. By adjusting a discharged amount using a gear pump as well as a speed of a belt conveyer so as to control a laminated amount, three kinds of nonwoven fabrics, that is, a nonwoven fabric C (density: 20 g/m$^2$, thickness: 200 μm), a nonwoven fabric D (density: 30 g/m$^2$, thickness: 300 μm), and a nonwoven fabric E (density: 45 g/m$^2$, thickness: 450 μm) were manufactured.

Hot Pressing-1

The nonwoven fabric A (density: 20 g/m$^2$, thickness: 200 μm) was subjected to pressing under conditions of 95° C. and 0.5 MPa (5 kgf) by a hot roll press machine so that front and back surfaces thereof were pressed once each. By so doing, a nonwoven fabric A2 having a thickness of 35 μm was obtained with its surfaces being flattened. Further, by treating the nonwoven fabric B (density: 35 g/m$^2$, thickness: 350 μm) in the same manner, a nonwoven fabric B2 having a thickness of 50 μm was obtained with its surfaces being flattened.

Hot Pressing-2

The nonwoven fabric D (density: 30 g/m$^2$, thickness: 300 μm) was subjected to pressing under conditions of 78° C. and 0.1 MPa (1 kgf) by a hot roll press machine so that front and back surfaces thereof were pressed once each, whereby its surfaces were flattened. Then, by subjecting this nonwoven fabric after the pressing to vacuum drying at 70° C. for 12 hours, residual monomers were removed, whereby a nonwoven fabric D2 (thickness: 100 μm) in which crystallization was promoted was obtained. Further, by treating the nonwoven fabric E (density: 45 g/m$^2$, thickness: 450 μm) in the same manner, a nonwoven fabric E2 (thickness: 200 μm) was obtained.

Integration with Gelatin Film

Each of the nonwoven fabrics thus obtained was cut into a rectangular shape that was 9 cm long in a lengthwise direction and 7 cm wide in a width direction, and an internal part (7 cm in the lengthwise direction and 5 cm in the width direction) was cut away, so that a nonwoven fabric in a rectangular frame shape having a width of each side portion of 1 cm was obtained (outer dimensions: 9 cm×7 cm, inner dimensions: 7 cm×5 cm).

Next, gelatin was dissolved in distilled water so that a 10 percent by weight (wt %) solution was obtained. The solution was cast in a petri dish (dimensions: 14 cm×10 cm), and the nonwoven fabric thus cut was placed thereon, so that the nonwoven fabric was impregnated with the gelatin solution. Then, the fabric was dried by air drying, whereby a complex composed of the nonwoven fabric and a gelatin film that were integrated with each other was obtained. The complex was cut so as to have a margin of the nonwoven fabric with a width of 5 mm at each side, and both surfaces were subjected to cross-linking by projecting ultraviolet rays thereto using a sterilization lamp (manufactured by Toshiba Corporation, GL-15, wavelength: 254 nm, power of UV lamp: 15 W, irradiation distance: 45 cm) for 10 hours each.

As to each complex obtained (antiadhesive material), the yarn threading tension was measured by the following method. Further, a gelatin film prepared in the same manner except that it was not complexed with a nonwoven fabric was used as a sample of a comparative example 1, and the foregoing nonwoven fabrics were used as samples of controls. As to these comparative example sample and control, the yarn threading tensions thereof were measured in the same manner as described above.

Measurement of the Yarn Threading Tension

A portion (5 mm×50 mm) of a laminate composed of the gelatin film and the nonwoven fabric was cut out of each of the foregoing complexes, and the portions thus cut out were used as samples. After each of the samples was immersed in physiological saline solution for 30 minutes, both ends of the sample in a lengthwise direction were fixed so that a distance between two chucks was 20 mm. Next, a 3-0 nylon suture with needle (Nesco Suture, ½ circle round-bodied needle) (trade name: Nesco Suture, manufactured by AZWELL Inc.) was threaded through the sample at a midpoint in the lengthwise direction and 2 mm from an edge in its width direction, and ends of the suture were fixed at a distance of 50 mm from the point at which the suture was threaded. Then, with the sample being maintained in the fixed state, the ends of the suture were pulled at a rate of 100 mm/min, and a maximal force (yarn threading tension) was measured using a measuring device (trade name: Instron 4302, manufactured by Instron Corporation). It should be noted that the measurement was carried out five times as to each sample, and an average value was determined. The results are shown in Table 1 below.

TABLE 1

| Material | | Density (g/m²) | With (+) or without (−) pressing | Maximal force (N) |
|---|---|---|---|---|
| (Complex with gelatin film) | | | | |
| Nonwoven fabric A | Poly-L-lactic acid | 20 | − | 0.581 |
| Nonwoven fabric A2 | Poly-L-lactic acid | 20 | + | 0.613 |
| Nonwoven fabric B | Poly-L-lactic acid | 35 | − | 0.845 |
| Nonwoven fabric B2 | Poly-L-lactic acid | 35 | + | 0.891 |
| Nonwoven fabric C | Copolymer | 20 | − | 0.210 |
| Nonwoven fabric D | Copolymer | 30 | − | 0.240 |
| Nonwoven fabric D2 | Copolymer | 30 | + | 0.266 |
| Nonwoven fabric E | Copolymer | 45 | − | 0.306 |
| Nonwoven fabric E2 | Copolymer | 45 | + | 0.353 |
| (Nonwoven fabric alone) | | | | |
| Nonwoven fabric D | Copolymer | 30 | − | 0.689 |
| Nonwoven fabric D2 | Copolymer | 30 | + | 0.695 |
| (Gelatin film alone) | | | | |
| Gelatin film | | − | − | 0.199 |

Copolymer: L-lactic acid-ε-caprolactone copolymer

It is seen in Table 1 that the complexes (antiadhesive materials) obtained by integration with the nonwoven fabrics had greater maximal forces as compared with the gelatin film as a comparative example 1, and therefore, they had an excellent suture property. Particularly in the case where the nonwoven fabric was made of poly-L-lactic acid, a greater maximal force was obtained. Further, it is seen that by increasing the density, a greater tension was obtained also. Still further, it also is found that by carrying out hot pressing, fuzzing of the nonwoven fabrics was decreased, and excellent integration with the gelatin films and greater maximal forces were achieved.

Example 2

Comparative Example 2

Antiadhesive materials (Examples 2-1 to 2-10) were prepared using reinforcing materials shown below, and functions thereof were evaluated. As Comparative Example 2, the same gelatin film as that of Comparative Example 1 was used, and the same evaluation was carried out. Fabric bodies used as reinforcing materials and methods for manufacturing the antiadhesive materials are shown below. It should be noted that each reinforcing material was cut into a rectangular shape of 9 cm in a lengthwise direction and 7 cm in a width direction, and an internal part (7 cm in the lengthwise direction and 5 cm in the width direction) was cut away, so that the reinforcing material in a rectangular frame shape such that each side portion had a width of 1 cm was used (outer dimensions: 9 cm×7 cm, inner dimensions: 7 cm×5 cm).

(A) Method for Manufacturing a Fabric Body

1. MB Nonwoven Fabric

In the same manner as that in the aforementioned "manufacture of nonwoven fabric-1" of Example 1, a nonwoven fabric was prepared by melt blowing, using poly-L-lactic acid as a material. The nonwoven fabric thus prepared had a thickness of 75 μm and a density of 35 g/m².

2. Plain Weave Fabric

A fabric body of plain weave fabric was obtained using a normally used weaving loom. It had a thickness of 160 μm and a density of 61 g/m².

3. Twin Loop Knit Fabric

Figure 7:
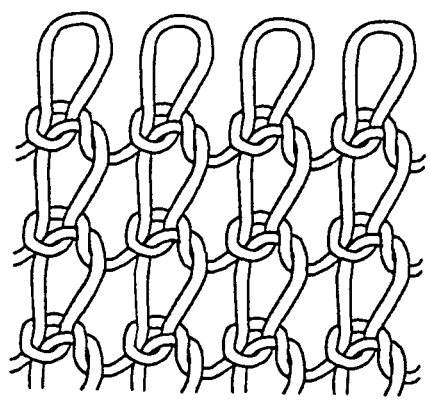
FIG. 7 is a diagram schematically illustrating a twin loop knit according to an example of an antiadhesive material of the present invention.

A twin loop knit fabric, prepared with a yarn having a thickness of 56 decitex (dtex), had a thickness of 215 μm, a loop density (vertical) of 13, a loop density (horizontal) of 12, and a density of 31 g/m². The loop density in the "vertical" direction refers to "the number of loops in 1.27 cm (½ inch) of the reinforcing material in the wale direction", and that in the "horizontal" direction refers to "the number of loops in the knitting machine circumferential direction" (this also applies hereinafter). The "dtex (decitex)" is a thickness unit according to the International System of Units (IS). FIG. 7 illustrates a schematic diagram of a knit stitch of a twin loop knit. It should be noted that the foregoing "circumferential direction" refers to a direction in which a cylinder and a dial of a knitting machine is rotated (course density) (this also applies hereinafter).

4. Smooth Knit Fabric (Interlock Knit Fabric)

This fabric was knitted by a 21-gauge smooth knitting machine. The smooth knit fabric, formed with a yarn thickness of 56 dtex, had a loop density (vertical) of 29, a loop density (horizontal) of 31.4, a thickness of 530 μm, and a density of 83 g/m². As the loop density (horizontal) in the circumferential direction of the smooth knit fabric, a sum of the number of loops on its front side that were formed by cylinder needles and the number of loops on its back side that were formed by dial needles is indicated. Besides, a sum of course loops was obtained as 15.7×2=31.4.

5. Plain Knit Fabric

This fabric was knitted by a 17-gauge circular knitting machine. The plain knit fabric, formed with a yarn thickness of 56 dtex, had a loop density (vertical) of 17, a loop density (horizontal) of 15, a thickness of 215 μm, and a density of 30 g/m².

6. High-gauge Plain Knit Fabric

This fabric was knitted by a 32-gauge high-gauge sinker knitting machine. The high-gauge plain knit fabric refers to a fabric knitted so as to have loops at a high density. The high-gauge plain knit fabric, formed with a yarn thickness of 56 dtex, had a loop density (vertical) of 28, a loop density (horizontal) of 18.4, a thickness of 215 μm, and a density of 43 g/m².

7. High-gauge Fraise Knit Fabric (Rib Knit Fabric)

This fabric was knitted by a 21-gauge fraise knitting machine. The high-gauge fraise, formed with a yarn thickness of 56 dtex, a loop density (vertical) of 27, a loop density (horizontal) of 30, a thickness of 310 μm, and a density of 62 g/m². It should be noted that as the loop density (horizontal) in the circumferential direction of the fraise knit fabric, a sum of the number of loops on its front side that were formed by cylinder needles and the number of loops on its back side that were formed by dial needles is indicated.

(B) Method for Manufacturing an Antiadhesive Material

Example 2-1

The MB nonwoven fabric, which was cut, was placed on a petri dish of the same kind as that of Example 1, and 10 wt % gelatin solution was cast thereon so that the fabric is impregnated with the gelatin solution. Then, it was subjected to air drying as it was, so that the nonwoven fabric and the gelatin film were integrated with each other. This complex was cut so as to have a margin of the nonwoven fabric with a width of 5 mm at each side, and both surfaces were subjected to cross-linking by projecting ultraviolet rays using a sterilization lamp (manufactured by Toshiba Corporation, GL-15, wavelength: 254 nm, power of UV lamp: 15 W, irradiation distance: 45 cm) for 10 hours each. The complex thus obtained was used as an antiadhesive material.

Example 2-2 to 2-5

In Examples 2-2, 2-3, 2-4, and 2-5, the plain weave fabric, the twin loop knit fabric, the smooth knit fabric, and the plain knit fabric were used, respectively, as reinforcing materials. First, in the same manner as that in Example 2-1, the reinforcing materials, which were cut, were placed in petri dishes, and the gelatin solution was cast thereon. They were subjected to air drying as they were, so that the reinforcing materials and the gelatin films were integrated with each other. They were subjected to cross-linking in the same manner as that in Example 2-1, whereby antiadhesive materials were prepared.

Example 2-6

A piece of the high-gauge plain knit fabric and two pieces of the MB nonwoven fabric that were obtained by the above-described method (A) for manufacturing a fabric body were laminated so that the former was interposed between the latter, and the laminate was subjected to pressing under conditions of 110° C. and 0.5 MPa (5 kgf) by a hot roll press machine so that front and back surfaces thereof were pressed once each. Using the obtained fabric as a reinforcing material, an antiadhesive material was prepared in the same manner as that in Example 2-2.

Example 2-7

A piece of the high-gauge plain knit fabric and two pieces of the MB nonwoven fabric that were obtained by the above-described method (A) for manufacturing a fabric body were laminated so that the former was interposed between the latter and were subjected to hot pressing in the same manner as that in Example 2-6, and an antiadhesive material was prepared from the foregoing laminate in the same manner as that in Example 2-2 except that the laminate was subjected further to a plasma treatment at room temperature, in oxygen gas at 67 Pa (0.5 torr), with 50 W, for 30 seconds.

Example 2-8

An antiadhesive material was prepared in the same manner as that in Example 2-7 except that the smooth knit fabric obtained by the above-described method (A) for manufacturing a fabric body was used in place of the high-gauge plain knit fabric.

Example 2-9

An antiadhesive material was prepared in the same manner as that in Example 2-7 except that the fraise knit fabric obtained by the above-described method (A) for manufacturing a fabric body was used in place of the high-gauge plain knit fabric.

(C) Evaluation of Functions of the Antiadhesive Materials
1. Suture Property and Separability (Non-Separability)

Figure 2:
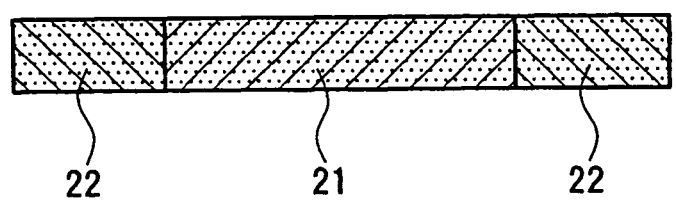
FIG. 2 is a cross-sectional view illustrating the antiadhesive material according to the foregoing example.
Figure 3:
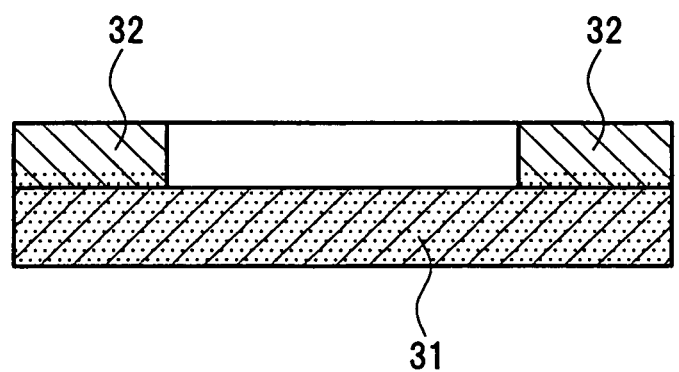
FIG. 3 is a cross-sectional view illustrating another example of an antiadhesive material of the present invention.
Figure 8:
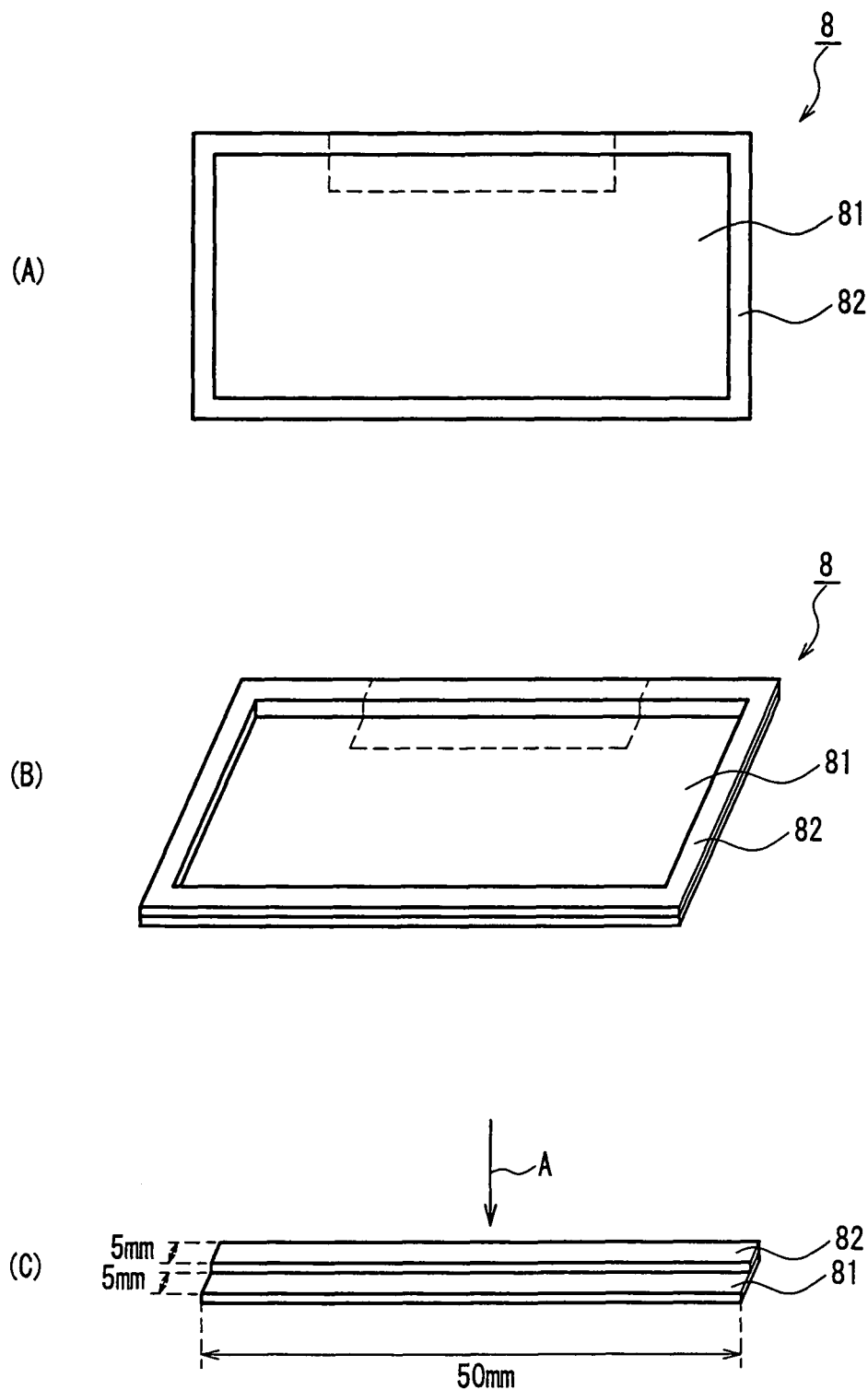
FIGS. 8A to 8C are views illustrating the antiadhesive material according to the foregoing example.

As shown in FIGS. 8A to 8C, a piece, 10 mm wide and 50 mm long, was cut out of each of the antiadhesive materials 8 thus prepared, and was used as a sample. FIG. 8A is a plan view of an antiadhesive material, FIG. 8B is a perspective view of the same, and FIG. 8C is a perspective view of a sample thus cut out of the antiadhesive material. It should be noted that in the drawings, the antiadhesive material is drawn as if there would be a level difference between a gelatin film 81 and the laminate portion in which a reinforcing material 82 and the gelatin film 81 were laminated, but this is a schematic illustration. Actually, it was, for instance, in a form as shown in FIG. 2 and hardly had such a level difference, since the gelatin solution was impregnated in the reinforcing material 82 as described above. Dotted lines in FIGS. 8A and 8B indicate the sample cut out thereof, and the sample was cut out so as to include both of the laminate portion including the gelatin film 81 and the reinforcing material 82 and the single layer portion of the gelatin film 81 alone. FIG. 8C shows the size of the sample. A view of the sample viewed in a direction indicated by an arrow A in FIG. 8C is a plan view of the sample. The sample thus cut out was immersed in physiological saline solution for 30 minutes.

Figure 9:
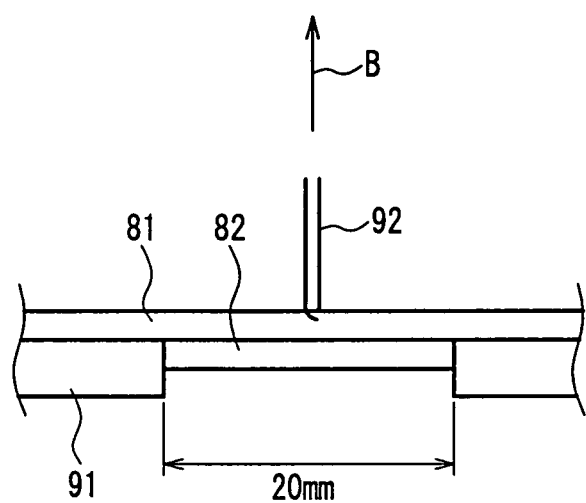
FIG. 9 is a plan view schematically illustrating a measurement state for evaluation of the property of being sutured (hereinafter referred to as suture property) and the separability of the antiadhesive material in the foregoing example.

Next, each sample thus immersed was set as shown in FIG. 9. FIG. 9 is a plan view of the sample thus set, which was obtained by viewing the sample in the direction indicated by the arrow A of FIG. 8C. First, as shown in the plan view of FIG. 9, both ends in a lengthwise direction of the single layer portion composed of the gelatin film 81 alone in the sample were fixed by a fixing member 91 so that a distance between two chucks was 20 mm. Next, a 3-0 nylon suture with needle (Nesco Suture, ½ circle round-bodied needle) (trade name: Nesco Suture, manufactured by AZWELL Inc.) (denoted with 92 in the drawing) was threaded through the sample at a midpoint in the lengthwise direction and 2 mm from an edge in its width direction in the lamination portion, and ends of the yarn were fixed at a distance of 50 mm from the point at which the yarn was threaded. Then, with the sample being maintained in the fixed state, the ends of the yarn were pulled at a rate of 100 mm/min in a direction indicated by an arrow B in FIG. 9 (width direction of the sample), and the suture property and the adhesivity of the reinforcing material and the gelatin at that time were observed. The results of the observation were evaluated according to the evaluation criteria shown below. It should be noted that in the case where a sample was evaluated as A to C, it is regarded as sufficiently applicable in practical use.

A (⊚): The portion composed of the gelatin film alone ruptured, and in the laminate portion composed of the gelatin film and the reinforcing material, neither rupture nor separation of the reinforcing material therefrom occurred.

B (○): In the laminate portion composed of the gelatin film and the reinforcing material, rupture or separation of the reinforcing material therefrom occurred when the tension was not less than 1 N.

C (△): In the laminate portion composed of the gelatin film and the reinforcing material, rupture or separation of the reinforcing material therefrom occurred when the tension was not less than 0.3 N.

D (X): In the laminate portion composed of the gelatin film and the reinforcing material, rupture or separation of the reinforcing material therefrom occurred when the tension was less than 0.3 N.

2. Strength of the Reinforcing Material

In the same manner as that in the evaluation of the suture property and the separability described above, each of the antiadhesive material was cut out into a size of 10 mm×50 mm, and was used as a sample. Both ends in a lengthwise direction of the single layer portion composed of the gelatin film 81 alone in the sample were fixed by the fixing member 91 so that a distance between two chucks was 20 mm. Next, a 3-0 nylon suture with needle (Nesco Suture, ½ circle round-bodied needle) (trade name: Nesco Suture, manufactured by AZWELL Inc.) (denoted with 92 in the drawing) was threaded through the sample at a midpoint in the lengthwise direction and 2 mm from an edge in its width direction in the lamination portion, and ends of the yarn were fixed at a distance of 50 mm from the point at which the yarn was threaded. Then, with the sample being maintained in the fixed state, the ends of the yarn were pulled at a rate of 100 mm/min in a direction indicated by an arrow B in FIG. 9 (width direction of the sample), and the tension upon rupture of the reinforcing material was observed. The results of the observation were evaluated according to the evaluation criteria shown below. It should be noted that in the case where a sample was evaluated as A to C in the following evaluation, it is regarded as sufficiently applicable in practical use.

A (⊚): The reinforcing material did not rupture even when the tension was not less than 2 N.
B (◯): The reinforcing material did not rupture even when the tension was not less than 1 N.
C (Δ): The reinforcing material did not rupture even when the tension was not less than 0.3 N.
D (X): The reinforcing material ruptured when the tension was less than 0.3 N.

2. Aipearance

An appearance of each reinforcing material before being integrated with the gelatin film was evaluated.

A (⊚): The reinforcing material was homogeneous without patterns.
B (◯): The reinforcing material had a fine surface texture, and a difference between a fiber density in a horizontal direction and that in a vertical direction was inconspicuous.
C (Δ): The reinforcing material had a fine surface texture, and a difference between a fiber density in a horizontal direction and that in a vertical direction was noticeable.
D (X): The reinforcing material had a coarse surface texture (fiber density: less than 10/cm).

The results of the function evaluation regarding the antiadhesive materials thus formed (2-1 to 2-9) are shown in Table 2 below. Further, the table 2 also shows the raw material (type of polymer) for the reinforcing material, the thickness of a yarn (unit: decitex (dtex)), the loop densities (vertical, horizontal), the thickness (μm), and the density (g/m$^2$). Regarding the reinforcing materials used in Examples 2-6 to 2-9, their thicknesses and densities after treatments (hot pressing, plasma treatment) are shown.

TABLE 2

| | | Constitution of reinforcing material | | | | | | Function evaluation | | |
|---|---|---|---|---|---|---|---|---|---|---|
| No. | Reinforcing material | Type of polymer | Thickness of yarn (dtex) | Loop density Vert. | Loop density Hrzn. | Thickness (μm) | Density (g/m$^2$) | Suture property, separability | Strength of reinforcing material | Appearance |
| Comp. Ex. 2 | Not used (gelatin film alone) | — | — | — | — | — | — | D | — | — |
| Ex. 2-1 | MB nonwoven fabric | PLLA | — | — | — | 75 | 35 | C | C | A |
| 2-2 | Plain weave fabric | PLLA | 56 | — | — | 160 | 61 | C | B | B |
| 2-3 | Twin loop knit | PLLA | 56 | 13 | 12 | 215 | 31 | B | B | C |
| 2-4 | Smooth (interlock) knit fabric | PLLA | 56 | 29 | 31.4 | 530 | 83 | B | A | C |
| 2-5 | Plain knit fabric | PLLA | 56 | 17 | 15 | 215 | 30 | B | B | C |
| 2-6 | High-gauge plain knit fabric + MB nonwoven fabric + hot pressing | PLLA | 56 | 28 | 18.4 | 113 | 65 | C | A | A |
| 2-7 | High-gauge plain knit fabric + MB nonwoven fabric + hot pressing + plasma treatment | PLLA | 56 | 28 | 18.4 | 113 | 65 | A | A | A |
| 2-8 | High-gauge smooth (interlock) knit fabric + MB nonwoven fabric + hot pressing + plasma treatment | PLLA | 56 | 29 | 31.4 | 153 | 103 | A | A | A |
| 2-9 | High-gauge fraise (rib) knit fabric + MB nonwoven fabric + hot pressing + plasma treatment | PLLA | 56 | 27 | 27 | 110 | 72 | A | A | A |

Antiadhesive materials sufficient for practical use could be prepared using reinforcing materials of various fabric bodies as indicated by Examples 2-1 to 2-9 shown in Table 2. It was found that among these reinforcing materials, particularly, reinforcing materials obtained by integrating the MB nonwoven fabric with the high-gauge plain knit fabric, the smooth knit fabric, or the fraise knit fabric and applying the plasma treatment had a considerably excellent suture property and the like.

From the results regarding Examples 2-6 and 2-7, it was found that the application of the plasma treatment to the reinforcing materials further improved the integration of the reinforcing material with the gelatin film, and improved the suture property (separability). Further, from the results regarding Examples 2-4 and 2-8, it also was found that in the case where a smooth knit fabric and a nonwoven fabric were integrated and subjected to the plasma treatment, the integration of gelatin and the reinforcing material was improved further, and the suture property was improved also.

INDUSTRIAL APPLICABILITY

As described above, the antiadhesive material of the present invention can be fixed surely to a predetermined site in a living body, and is capable of preventing usual adhesion of tissues effectively. Further, in the case where it is formed in a cylindrical shape, it can be used as an antiadhesive material for a tendon, a nerve, etc., or as an induction tube for a nerve. Then, after it finishes performing the function of preventing adhesion, it is degraded and absorbed in the living body. Therefore, it does not cause any problem concerning safety.

The invention claimed is:

1. An antiadhesive material comprising a gelatin film, the antiadhesive material further comprising:
    a reinforcing material that is made of a biodegradable polymer other than collagen and is arranged in the gelatin film,
    wherein the reinforcing material is a fabric body having a density in a range of 5 g/m$^2$ to 45 g/m$^2$ and a yarn threading tension in a range of 0.210 N to 200 N, and
    wherein the biodegradable polymer is at least one polymer selected from the group consisting of polylactic acid, lactic acid-caprolactone copolymer, polyglycolic acid, lactic acid-glycolic acid copolymer, lactic acid-ethylene glycol copolymer, polydioxanon, glycolic acid-caprolactone copolymer, glycolic acid-trimethylene carbonate copolymer, glycolic acid-dioxanon-trimethylene carbonate copolymer, chitin, chitosan, and fibrin,
    wherein the reinforcing material and the gelatin film are integrated due to gelation of gelatin that has intruded entirely in an internal part of the reinforcing material, and
    wherein the fabric body is a knitted fabric that is a twin loop knit fabric having the twin loop knit as shown in FIG. 7.

2. The antiadhesive material according to claim 1, wherein the antiadhesive material is in a sheet form or in a cylindrical form.

3. The antiadhesive material according to claim 1, wherein the reinforcing material is arranged in a portion of the gelatin film to be subjected to suturing.

4. The antiadhesive material according to claim 1, wherein the reinforcing material is arranged along a periphery of the gelatin film.

5. The antiadhesive material according to claim 1, wherein the fabric body is integrated with a nonwoven fabric to form a complex.

6. The antiadhesive material according to claim 5, wherein the nonwoven fabric is manufactured by at least one method selected from the group consisting of melt blowing, needle punching, spunbonding, and flash spinning.

7. The antiadhesive material according to claim 6, wherein the nonwoven fabric is processed by hot pressing.

8. The antiadhesive material according to claim 1, wherein the fabric body has a thickness in a range of 10 µm to 1000 µm.

9. The antiadhesive material according to claim 1, wherein the fabric body has a yarn threading tension in a range of 0.3 N to 200 N.

10. The antiadhesive material according to claim 1, wherein the biodegradable polymer is at least one polymer selected from the group consisting of polylactic acid, lactic acid-caprolactone copolymer, and polyglycolic acid.

11. The antiadhesive material according to claim 10, wherein a molar ratio (A:B) of lactide (A) and caprolactone (B) in the lactic acid-caprolactone copolymer is in a range of 85:15 to 40:60.

12. The antiadhesive material according to claim 1, wherein the reinforcing material is subjected to a hydrophilicity imparting treatment.

13. The antiadhesive material according to claim 12, wherein the hydrophilicity imparting treatment is at least one treatment selected from the group consisting of plasma treatment, glow discharge treatment, corona discharge treatment, ozone treatment, graft treatment, coating, chemical treatment, and ultraviolet irradiation.

14. The antiadhesive material according to claim 1, wherein the gelatin film is a cross-linked film.

15. The antiadhesive material according to claim 14, wherein the gelatin film is cross-linked by at least one method selected from the group consisting of ultraviolet treatment, heat treatment, and chemical cross-linking agent treatment.

16. The antiadhesive material according to claim 14, wherein the gelatin film is cross-linked under conditions of an ultraviolet lamp of 4 W to 40 W, an irradiation time of 0.1 hour to 100 hours, and an irradiation distance of 5 cm to 100 cm.

17. The antiadhesive material according to claim 1, wherein a time of presence of the gelatin film in a living body is in a range of 12 hours to 90 days.

18. The antiadhesive material according to claim 1, wherein the gelatin film has a thickness in a range of 20 µm to 2000 µm.

19. The antiadhesive material according to claim 1, wherein a concentration of endotoxin contained in the gelatin is not more than 200 EU/g.

20. The antiadhesive material according to claim 1, wherein the knitted fabric is a piece of knitted fabric, and the piece of knitted fabric forms a complex with two pieces of non-woven fabric, in which the piece of knitted fabric is interposed between the two pieces of nonwoven fabric.

* * * * *